United States Patent
Prins et al.

(10) Patent No.: US 11,359,231 B2
(45) Date of Patent: *Jun. 14, 2022

(54) BIOSENSOR BASED ON A TETHERED PARTICLE

(71) Applicant: Technische Universiteit Eindhoven, Eindhoven (NL)

(72) Inventors: Menno Willem José Prins, Rosmalen (NL); Maarten Merkx, Best (NL); Leonardus Josephus van Ijzendoorn, Eindhoven (NL); Peter Zijlstra, Utrecht (NL); Emilius Willem Adriaan Visser, Mississauga (CA); Max Rose-Marie Wilhelmus Scheepers, Heerlen (NL)

(73) Assignee: Technische Universiteit Eindhoven, Eindhoven (NL)

( * ) Notice: Subject to any disclaimer, the term of this patent is extended or adjusted under 35 U.S.C. 154(b) by 90 days.

This patent is subject to a terminal disclaimer.

(21) Appl. No.: 16/724,253

(22) Filed: Dec. 21, 2019

(65) Prior Publication Data

US 2020/0140932 A1 May 7, 2020

Related U.S. Application Data

(63) Continuation of application No. 15/536,866, filed as application No. PCT/EP2015/079864 on Dec. 15, 2015, now Pat. No. 10,519,486.

(Continued)

(51) Int. Cl.
*G01N 33/543* (2006.01)
*C12Q 1/6825* (2018.01)
(Continued)

(52) U.S. Cl.
CPC .......... *C12Q 1/6825* (2013.01); *G01J 3/4412* (2013.01); *G01N 33/542* (2013.01);
(Continued)

(58) Field of Classification Search
CPC ............ C12Q 1/6825; C12Q 2563/149; G01N 33/543; G01N 33/54326; G01N 33/54353;
(Continued)

(56) References Cited

U.S. PATENT DOCUMENTS

2012/0184048 A1 7/2012 Van Ommering et al.
2017/0315115 A1* 11/2017 Prins .................. G01N 33/6872

FOREIGN PATENT DOCUMENTS

WO WO-2009061783 A2 * 5/2009 .......... B01J 19/0046

OTHER PUBLICATIONS

Li Deng et al, "An off-on-off electrochemiluminescence approach for ultrasensitive detection of thrombin", Biosensor and Bioelectronics 59 (2014) 58-63) (Year: 2014).*

(Continued)

*Primary Examiner* — Christopher L Chin
(74) *Attorney, Agent, or Firm* — Casimir Jones, S.C.; Tanya A. Arenson

(57) ABSTRACT

A method for sensing an analyte uses tethered particle motion. A functionalized particle has a first state in which the functionalized particle is bound to the surface and a second state in which the functionalized particle is not bound to the surface, where the functionalized particle switches between the first and second states depending on the presence and absence of the analyte, thereby changing motion characteristics of the functionalized particle depending on the presence of the analyte. A spatial coordinate parameter of the functionalized particle is measured by a detector, and a processor determines the presence/concentration of the analyte from changes in the measured spatial coordinate parameter.

20 Claims, 7 Drawing Sheets

Related U.S. Application Data

(60) Provisional application No. 62/092,751, filed on Dec. 16, 2014, provisional application No. 62/092,763, filed on Dec. 16, 2014, provisional application No. 62/132,096, filed on Mar. 12, 2015.

(51) Int. Cl.
*G01N 33/542* (2006.01)
*G01J 3/44* (2006.01)
*G01N 21/63* (2006.01)

(52) U.S. Cl.
CPC ....... *G01N 33/543* (2013.01); *G01N 33/5436* (2013.01); *G01N 33/54326* (2013.01); *G01N 33/54353* (2013.01); *G01N 33/54373* (2013.01); *C12Q 2563/149* (2013.01); *G01N 21/63* (2013.01)

(58) Field of Classification Search
CPC .............. G01N 33/542; G01N 33/5436; G01N 33/54373; G01N 21/63; G01N 33/54313; G01N 2600/00; G01J 3/4412
USPC ............ 435/287.2, 288.7; 436/518, 164, 805
See application file for complete search history.

(56) References Cited

OTHER PUBLICATIONS

Longhua Guo et al, "Distance-Mediated Plasmonic Dimers for Reusable Colorimetric Switches: A Measurable Peak Shift of More than 60 nm", Small vol. 9(2), (2013) 234-240) (Year: 2013).*

Blumberg, et al., Three-dimensional characterization of tethered microspheres by total internal reflection fluorescence microscopy. Biophys J. Aug. 2005;89(2):1272-81.

Bruls, et al., Rapid integrated biosensor for multiplexed immunoassays based on actuated magnetic nanoparticles. Lab Chip. Dec. 21, 2009;9(24):3504-10.

Heo et al., Towards smart tattoos: implantable biosensors for continuous glucose monitoring. Adv Healthc Mater. Jan. 2013;2(1):43-56.

Laurens, et al., Dissecting protein-induced DNA looping dynamics in real time. Nucleic Acids Res. Sep. 2009;37(16):5454-64.

* cited by examiner

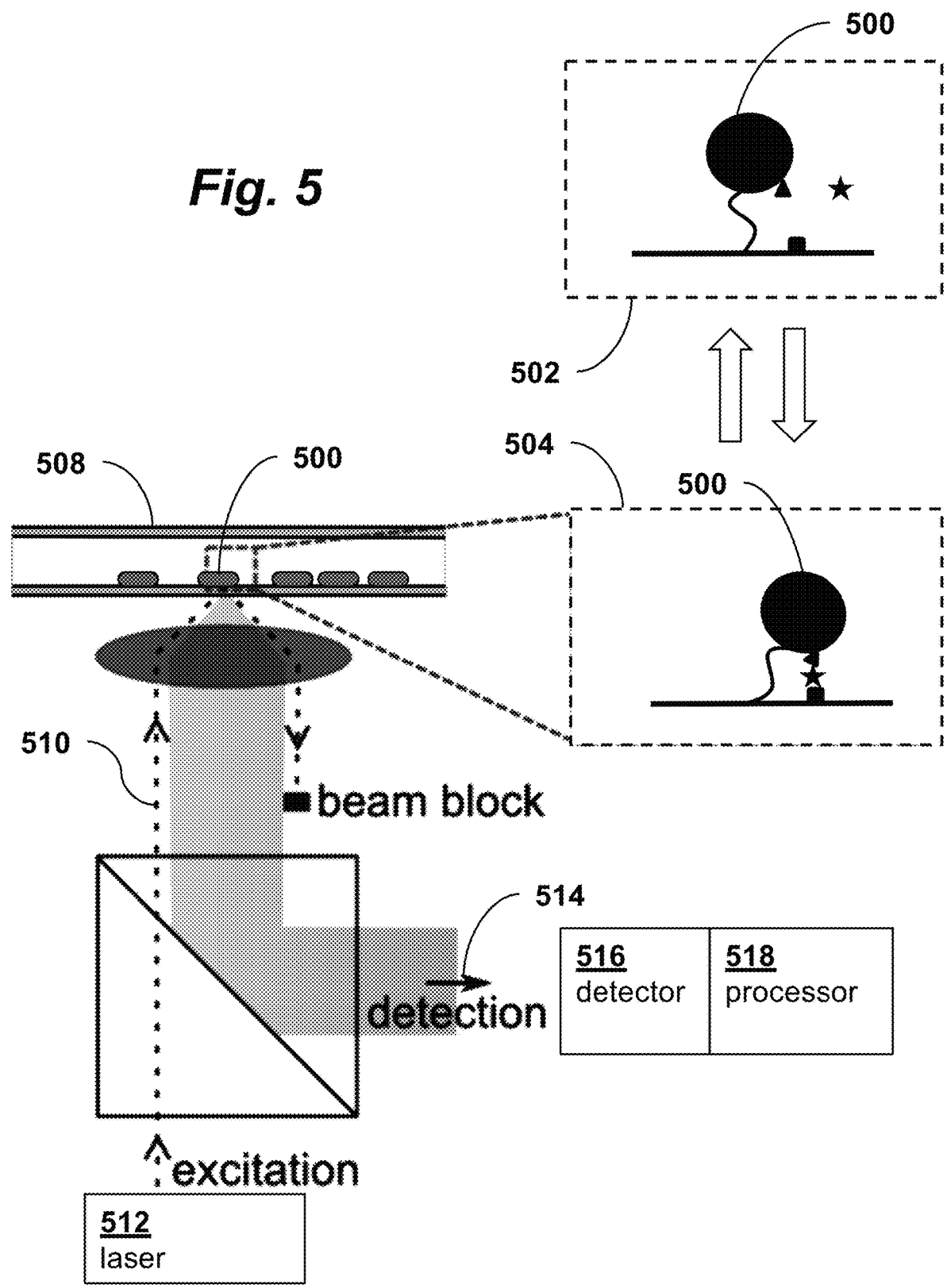

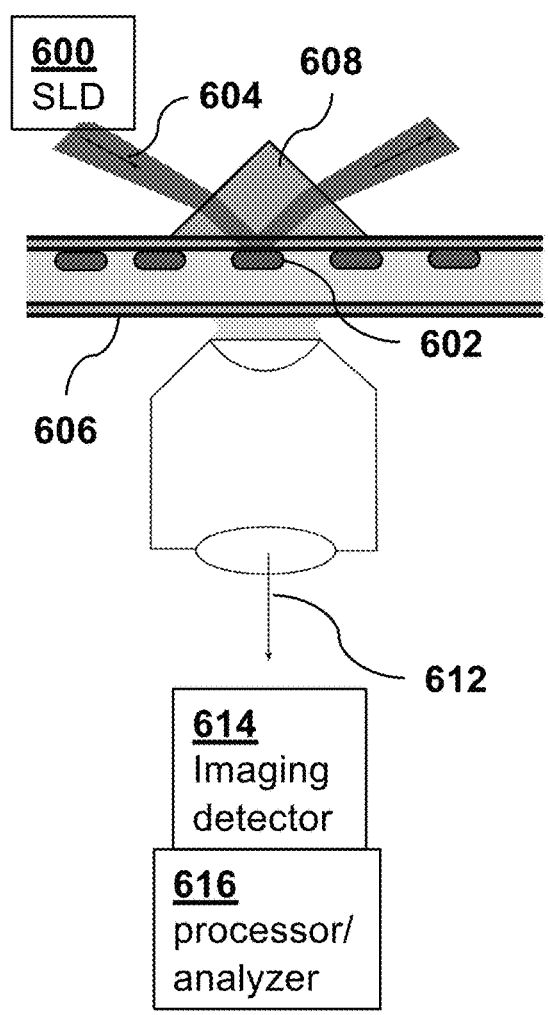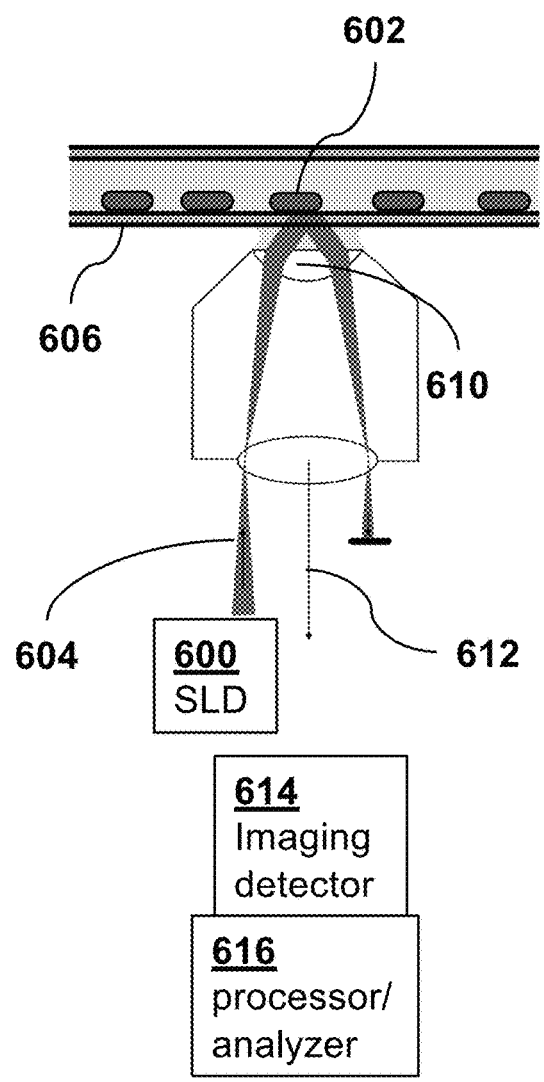

Fig. 7
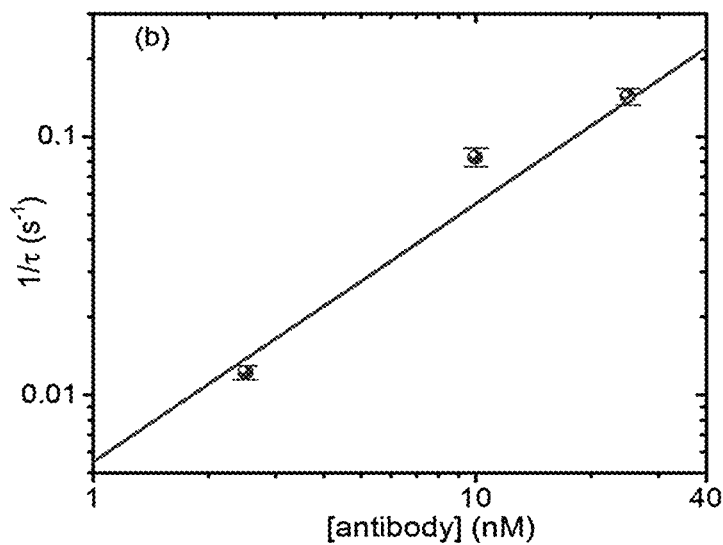
Fig. 8A             Fig. 8B
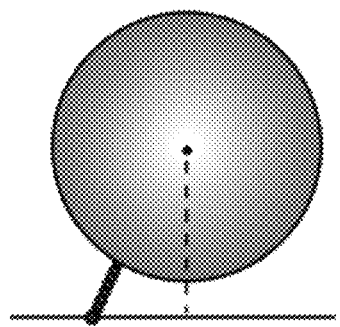   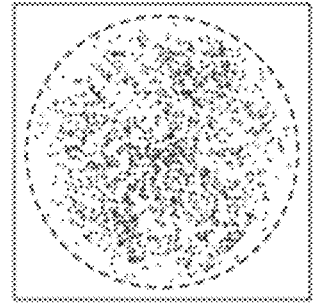
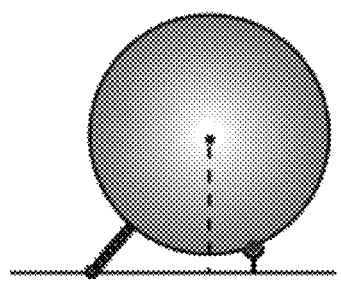   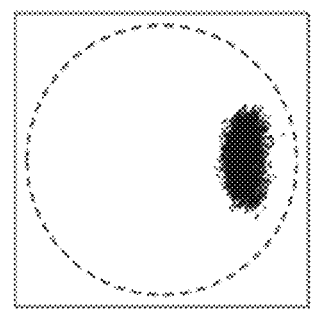
Fig. 8C             Fig. 8D

BIOSENSOR BASED ON A TETHERED PARTICLE

FIELD OF THE INVENTION

The present invention relates generally to a biosensor technique based on detecting the presence of an analyte based on changes in motion of a functionalized particle attached by a tether to a surface.

BACKGROUND OF THE INVENTION

Most biosensing principles for biochemical markers have been developed for use in in-vitro diagnostics, where a sample is taken (e.g., blood, saliva, urine, mucus, sweat or cerebrospinal fluid) and is transferred to an artificial device (e.g., a plastic disposable) outside a living organism. In such biosensing assays, a wide range of sample pre-treatment steps can be applied (e.g., separation or dilution steps) and multiple reagents can be introduced in the assay (e.g., for target amplification, signal amplification, or washing steps). Examples of in-vitro biosensing assays are: immunoassays, nucleic acid tests, tests for electrolytes and metabolites, electrochemical assays, enzyme activity assays, cell-based assays, etc. (see Tietz, Textbook of Clinical Chemistry and Molecular Diagnostics, 2005).

In in-vivo biochemical sensing, at least a part of the sensor system remains connected to or is inserted in the human body, e.g., on the skin, or in the skin, or below the skin, or on or in or below another part of the body. Due to the contact between the biosensor and the living organism, in-vivo biochemical sensing sets high requirements on biocompatibility (e.g., inflammation processes should be minimized) and the sensor system should operate reliably within the complex environment of the living organism. For monitoring applications, the system should be able to perform more than one measurement over time and the system should be robust and easy to wear.

An important application of in-vivo biochemical sensing is continuous glucose monitoring (CGM). Commercial continuous glucose monitoring devices are based on enzymatic electrochemical sensing (see e.g., Heo and Takeuchi, Adv. Healthcare. Mat. 2013, vol. 2, p. 43-56). Enzymatic sensing is less generic than affinity-based sensing. Commercial systems for in-vivo glucose monitoring are available from Dexcom and Medtronic. A disadvantage of present-day CGM systems is that the sensor response shows drift, and therefore the systems require regular recalibration by an in-vitro blood glucose test (for a review, see e.g., Heo and Takeuchi, Adv. Healthcare. Mat. 2013, vol. 2, p. 43-56).

Several particle-based biosensing techniques are known in the art, including techniques based on detection by optical scattering, e.g., Bruls et al., Lab Chip 2009. Patent application US2012184048 describes a method for the characterization of different bond types in a particle-based biosensing system. Unbound particles bind to a sensing surface in a target-dependent manner, thereafter a bound-free separation is performed (a wash step), and subsequently fluctuations in the intensity of light scattered from the bound particles are measured in order to characterize the bond type, e.g., to discriminate between specifically and non-specifically bound particles. The use of unbound particles and a bound-free separation process is useful for in-vitro diagnostics. However, for in-vivo applications, unbound particles may pose a safety risk, and it is difficult to implement a bound-free separation process in an in-vivo situation.

The above difficulty can be avoided by biosensing techniques based on tethered particle motion (TPM). The TPM technique is based on measurements of the motion of particles tethered to a surface. An example is Laurens et al., Nucleic Acids Res. September 2009; 37(16): 5454-5464, where TPM experiments are reported on proteins that bind to a DNA tether, in order to reveal how the proteins change the DNA conformation. In such studies, measures are taken to avoid not-via-the-tether binding of the particle to the surface, because a particle that is bound to the surface in another way than via the tether, does not give information about the tether. An example is: Blumberg et al., Biophysical Journal 2005; 89, 1272-1281.

Biosensors having functionalized tethers attached to a surface have been developed based on the principle that the motion of particles attached by a tether changes in dependence upon presence of analyte. The motion changes are due to changes in the structure of the tether itself due to the presence of the analyte. There are also techniques for detecting analytes by measuring a kinematic property of a functionalized particle tethered to a surface in dependence upon presence of analyte. In these techniques, it is important to avoid particle bonding to the surface, because the steric hindrance interferes with sensitivity influenced by the analyte.

SUMMARY OF THE INVENTION

In one aspect, the present invention provides a biosensing technique based on detecting changes in motion of a functionalized particle attached by a tether to a surface, where the presence of an analyte changes the particle between bound and unbound states to the surface. In contrast with known tethered particle based biosensing techniques where binding to the surface is undesired, according to the present invention the analyte causes the tethered particle to change between bound and unbound states with the surface. This is a surprising contrast with conventional wisdom in tethered particle motion studies that explicitly teach that binding to the surface is to be avoided.

The present invention provides a biosensing technology for in-vivo biochemical monitoring that is sensitive, specific, stable, biocompatible, and flexible. There are many applications of this biosensing technique, including continuous glucose monitoring for diabetic patients, without the need to regularly recalibrate the sensor system; electrolyte and metabolite monitoring, that is important for patients that may become unstable, e.g., in critical care; electrolyte measurements that are helpful to monitor kidney function, e.g., in cardiac patients; protein measurements that can be helpful to monitor cardiac function, e.g., BNP is a key marker for heart failure; drug and/or drug metabolite measurements that are helpful to monitor drug intake (compliance) and pharmacokinetics (aiming to keep the drug within the desired concentration window); drug response measurements that are helpful to monitor drug effectiveness; and monitoring for disease management, therapy control, compliance monitoring. In addition, the method may also be applied very generally for molecular biosensing, e.g., for in-vitro diagnostics, point-of-care testing, environmental testing, food testing, forensics, etc. The current invention may also find application in biological, biomedical and pharmaceutical research, e.g., to monitor assays with live cells, tissue, organs, etc. Analytes can be electrolytes, small molecules, lipids, carbohydrates, peptides, hormones, proteins, oligonucleotides, DNA, RNA, etc.

In one aspect, the invention provides a method for sensing an analyte using tethered particle motion. The method includes bringing a matrix containing the analyte into contact with a sensor device having a surface and a tether molecule bound at a first end to the surface and bound at a second end to a functionalized particle. The functionalized particle has a first state in which the functionalized particle is bound to the surface and a second state in which the functionalized particle is not bound to the surface, where the functionalized particle switches between the first and second states depending on the presence and absence of the analyte, thereby changing motion characteristics of the functionalized particle depending on the presence of the analyte. The method includes measuring a spatial coordinate parameter of the functionalized particle relative to the surface, and determining the presence/concentration of the analyte from changes in the measured spatial coordinate parameter.

The spatial coordinate parameter may, in some embodiments, be measured by illuminating the functionalized particle and/or the surface, detecting optical radiation from the functionalized particle and/or the surface, and determining from the optical radiation the position, orientation, and/or velocity of the functionalized particle with respect to the surface.

The spatial coordinate parameter may, in some embodiments, be measured by exciting free charge carriers in the functionalized particle and/or the surface, and detecting optical radiation from the functionalized particle and/or the surface, where the exciting and/or detecting is performed at a wavelength near a plasmon resonance of the functionalized particle and/or the surface. The presence/concentration of the analyte may be determined by determining changes in the detected optical radiation. The exciting of free charge carriers may be performed by excitation with optical light from a light source with a line width larger than 5 nm or from a superluminescent diode.

In some embodiments, the presence/concentration of the analyte may be determined from changes in a distribution of particle localizations, a change of the area of a pattern of localizations, or a change of the step sizes between particle localizations.

In some embodiments, the presence/concentration of the analyte may be determined by performing histogram and/or histogram processing to suppress background noise and enhance specificity.

BRIEF DESCRIPTION OF THE DRAWINGS

FIG. 5 is a schematic diagram of a system for sensing the presence of a target analyte using optical excitation and detection of plasmon resonance shifts in tethered nanoparticles, according to an embodiment of the present invention.

FIGS. 6A-B illustrate two implementations of a combined microscopy and spectroscopy method, according to embodiments of the present invention.

FIG. 7 is a graph of mean binding rate vs. analyte concentration according to a power law, according to an embodiment of the present invention.

FIGS. 8A-B show a schematic diagram of an unbound tethered particle and a plot x-y plane positions of the unbound tethered particle during a sampling period, respectively, according to an embodiment of the invention.

FIGS. 8C-D show a schematic diagram of a bound tethered particle and a plot x-y plane positions of the bound tethered particle during a sampling period, respectively, according to an embodiment of the invention.

DETAILED DESCRIPTION

Embodiments of the present invention are motivated by several insights related to the design of biosensors for in-vivo applications: (i) it is beneficial to use particles because of their detectability, stability, and biofunctionalization options, (ii) it is beneficial to use tethered particles rather than unbound particles, and (iii) it can be beneficial that the tether functionality and the binding functionality are separated in the biosensing technique.

According to embodiments of the present invention, a tethered-particle technique is provided in which the interaction of the particle with the surface plays a central role. The function of the tether is to keep the particle close to the surface, and it is a measurement of the target-modulated interaction between the particle and the surface that yields biological sensing information.

Figure 1:
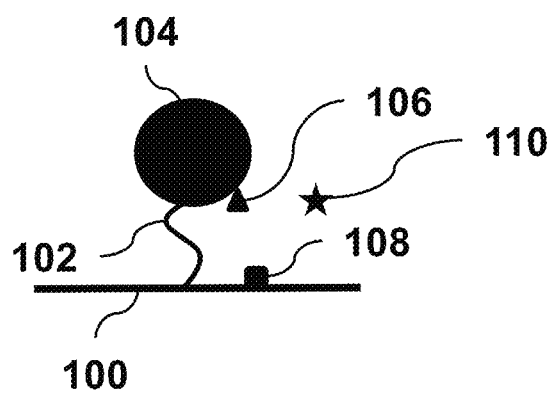
FIG. 1 is a schematic illustration of the basic components of a tethered particle biosensing technique, according to an embodiment of the invention.
Figure 2A:
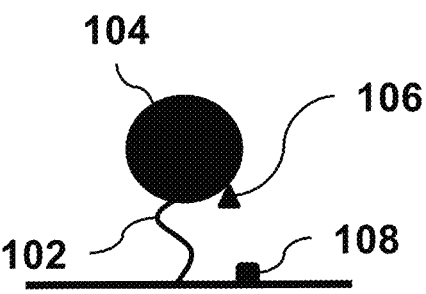
FIGS. 2A-B is a schematic illustration of unbound and bound states of a tethered particle biosensing technique, according to an embodiment of the invention.
Figure 2B:
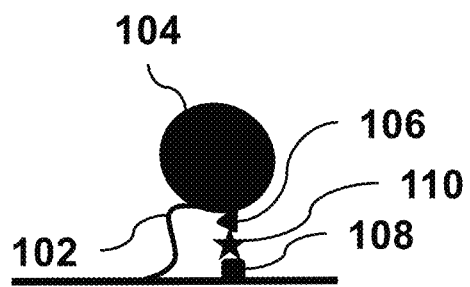

The basic components of a biosensing technique according to an embodiment of the invention is illustrated in FIG. 1. A biosensor device has a surface 100 exposed to a matrix containing a target analyte 110. A tether molecule 102 is bound at a first end to the surface 100 and bound at a second end to a particle 104 functionalized with a moiety 106. The surface 100 is functionalized with another moiety 108. Alternatively, either moiety 106 or moiety 108 can be conjugated to the tether. The functionalization of both moieties is selected such that the target analyte 110 will bond with them. The conjugation and linkage of the moieties to the particle and to the substrate is done in such a way that the moieties have analyte-specific biological binding activity. FIGS. 2A-B illustrate two states of the system of FIG. 1, which depend on the presence of the target analyte 110. In the state shown in FIG. 2A, the analyte 110 is not present and the tethered particle 104 is free to move, with limitation by the tether. In the state shown in FIG. 2B, the analyte 110 is present, and binds to moiety 106 and 108, resulting in the tethered particle 104 binding to the surface 100. Consequently, the motion of the functionalized particle 104 changes between a bound state and unbound state, depending on the presence of the analyte 110. In case either moiety 106 or moiety 108 is conjugated to the tether, then a binding of analyte 110 to moieties 106 and 108 changes the motion of the functionalized particle 104, between a state with more motional freedom (named 'unbound', or 'particle not bound to the surface') and a state with less motional freedom (named 'bound', or 'particle bound to the surface').

In an example implementation of this embodiment, target analytes 110 with two epitopes may be measured with antibodies or fragments thereof coupled to the particle 104 and to the substrate 100. Alternatively, antibody detection can be enabled when moiety 106 and moiety 108 represent antibody-specific epitopes (e.g., peptide epitopes, mimitopes) or native proteins, so that the antibody can form a sandwich complex (FIG. 2B) by the binding of its two antigen binding domains to moiety 106 and moiety 108. Alternatively, binding of the molecular pair (moiety 106 and moiety 108) can be induced by analyte (as metal binding between two metal binding domains, or ligand induced cofactor recruitment in nuclear receptor ligand binding domains).

Figure 3A:
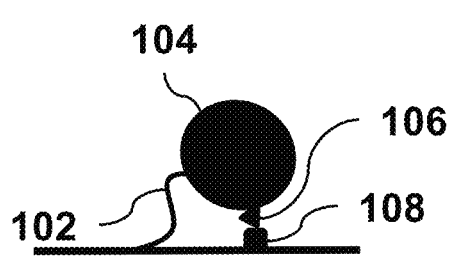
FIGS. 3A-B is a schematic illustration of unbound and bound states of a tethered particle biosensing technique, according to an embodiment of the invention.
Figure 3B:
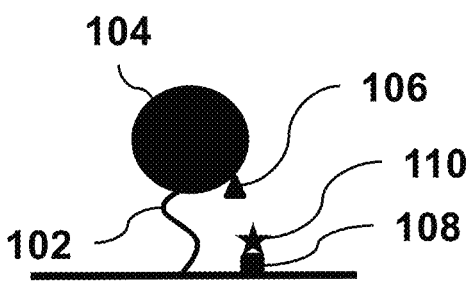

Another embodiment of the invention is illustrated in FIGS. 3A-B. In this embodiment, moiety 106 and moiety 108 are selected to bind to each other when the target analyte 110 is not present, as shown in FIG. 3A, so that the tethered particle 104 is in a bound state. In the presence of the target analyte, moiety 106 and moiety 108 do not bind to each other, due to preferential binding with analyte instead, as shown in FIG. 3B, so that the tethered particle 104 is in an unbound state. Moiety 106 and moiety 108 can be an analyte-binding molecule and an analyte-analogue.

In an example implementation of this embodiment, target analytes 110 with one epitope may be measured, e.g., with at least one specific capture molecule on the particle and a target-analogue on the substrate, or vice versa.

Figure 4A:
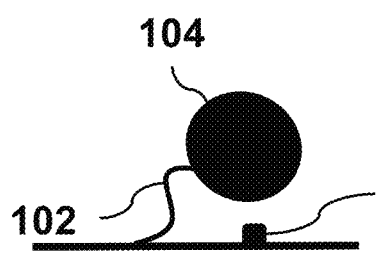
FIGS. 4A-B is a schematic illustration of unbound and bound states of a tethered particle biosensing technique, according to an embodiment of the invention.
Figure 4B:
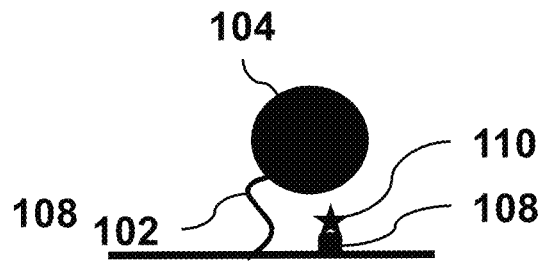

According to another embodiment shown in FIGS. 4A-B, moiety 106 is not included. In this embodiment, target analyte 110 induces changes in steric hindrance of the particle 104. In the state shown in FIG. 4A, where the analyte is not present, tethered particle 104 is in a less-hindered state. In the state shown in FIG. 4B, tethered particle 104 is in a more-hindered state, as a result of the binding of analyte 110 to moiety 108. In a variation of this embodiment, the moiety 108 is not included and the moiety 106 is included instead, with the principle of operation otherwise being the same.

In an example implementation of this embodiment, target analytes 110 may be measured via steric hindrance, where the binding of target to the particle and/or the substrate changes the parameter space that is accessible by the particle.

In any of the embodiments of the invention, detection of an analyte may also be performed indirectly through a cascade of intermediate reactions. For example, an enzyme reacts with the analyte and generates a product, which reacts with a biochemical moiety on the particle and/or the substrate surface, and thereby changes a coordinate parameter of the colloido-molecular particle-tether-surface system. In the context of the present description, the detection of an analyte may be direct or indirect, and in the case of an indirect detection, the analyte-generated product plays the role of the analyte being detected.

Generally, in a biosensing device for the detection of analyte in fluid or other matrix according to embodiments of the invention, the device includes at least two objects (i.e., surface and particle, where the surface may also be embodied as a particle) connected by at least one tether. The tether keeps the two objects close together, which is advantageous for the encounter frequency and effective concentration, and for accurate optical detection.

The particle preferably has a longest dimension smaller than 5 micrometers. More preferably, the particle diameter is in the range between 3 nm and 5 μm. Preferred particles have strong optical properties, such as, e.g., gold nanoparticles with plasmonic resonance properties, or particles with strong fluorescence or scattering properties. Examples of suitable particle materials are organic materials (e.g., polymer), inorganic materials (e.g., silica), metals (e.g., gold), or combinations thereof.

Advantages of using particles include stability and high optical signals. At least one of the two objects is provided with at least one biochemical moiety on its surface. The biochemical moieties give biochemical specificity to the objects.

In operation, a coordinate parameter is measured representative of the relative position of the two objects with respect to each other. Without loss of generality, embodiments may be described in the rest frame of one object (i.e., the surface) with the other object (i.e., particle) being described as being in motion. The surface may also be a curved surface, convex or concave, e.g., the surface of a particle. The analyte, when present, binds to one or both of the two objects, altering the possible motions of the tethered particle. Consequently, a property of the spatial coordinate parameter changes in the presence of the analyte. Thus, the presence and/or concentration of analyte is determined from a measured change of the property of the coordinate parameter.

The spatial coordinate parameter can be, for example, the position of the particle in space (xyz), the orientation of the particle relative to the surface, and/or their time dependencies, including their time derivatives, such as angular velocity of the particle and linear velocity of the particle. A property of the coordinate parameter can be, for example, a property of the spatial and/or velocity distribution function. Preferably, a coordinate parameter and a change of the coordinate parameter of the at least two objects with respect to each other are measured optically.

Preferably the detection is performed with single-particle resolution, in order to be able to independently measure the time-dependent behavior of the different particles. This will allow one to perform signal processing on independent particles (e.g., to make histograms of bound and unbound states) and to apply filtering algorithms (e.g., to separate specific and non-specific binding) with high statistics. Single-molecule resolution allows high sensitivity and detection of low concentrations. When the fundamental single-molecule limit is reached, then maximum data is collected from the molecular binding and/or conversion process, giving optimal statistics and optimal precision.

Preferably the device includes an array of tethered particles on the same surface, so as to gather statistics and thereby improve reliability, sensitivity, and speed.

Embodiments may also include anti-fouling coatings, gel biosensing, a neutralization layer, filtering function, a selective permeation layer, spatial multiplexing, particle-based multiplexing, calibration, controls, optical detection possibilities. Embodiments may include measures to block and reduce unwanted processes, and to increase efficiency, stability, and selectivity of signal generation.

Embodiments of the invention will allow for the real-time probing of analyte concentrations in complex fluids (e.g., blood, saliva, interstitial skin fluid). Single-molecule resolution should be achievable, for high analytical sensitivity. Furthermore, high specificity may be reached by isolating specific from the non-specific interactions. This may allow direct real-time series of measurements in complex fluids, ideally without repeated sample taking or intermediate filtering steps.

An important advantage of the proposed biosensor is that it is based on biochemical affinity, which makes it generic and enables a wide variety of possible assays.

In one specific implementation, the sensing system may be used to perform continuous analyte monitoring such as glucose monitoring, e.g., in a competitive format with a glucose binding protein on the particle or on the substrate (e.g., an apo-glucose oxidase, or a periplasmic transport protein, or another glucose-binding molecule).

Commercial applications of the invention include in-vivo biosensing, but also in-vitro biosensing. Embodiments of the invention can be applied in the development of next generations of biosensors based on particle labels and having single-particle and single-molecule resolution.

Alternatively, the sensing device may be part of a feedback system during a medical procedure, e.g., a sensor on or in an endoscope, a tube, a needle, a fiber, a catheter, a patch.

The biosensing technique is also relevant for in-vitro diagnostic testing, particularly for point-of-care testing, where it is advantageous if a specific molecular binding process leads to a signal that is detectable by optical means, with little further chemical/biochemical/fluidic processing.

In another aspect of the invention, the sensing technology is used for in-vivo, ex-vivo, or in-vitro applications. In another aspect of the invention, the sensing technology is used for applications on human subjects, or on non-human subjects, e.g., in veterinary applications or for testing of other biological systems. In another aspect of the invention, the sensing technology is part of a disposable probe that is in contact with the subject or with the biological system.

In another aspect of the invention, the sensing technology involves a disposable cartridge, e.g., a lab-on-a-chip cartridge, or a disposable used in laboratory-based testing, or another disposable such as a tube, a needle, a fiber, a catheter, a patch. In another aspect of the invention, the disposable or the probe or the cartridge is attached to an instrument or an analyzer in order to power and/or actuate and/or read out the disposable, the probe or the cartridge. In another aspect of the invention, the instrument is suited for processing signals from the probe or cartridge, and/or for communicating data between the instrument and the probe or cartridge, and/or for communicating data between the instrument and e.g., an information system or communication network.

The sensing system may be part of a disease management system, which may include (bio)chemical and/or physical sensing, a system for data collection and processing, and a system for physical and/or (bio)chemical actuation. The system may be connected in a closed-loop format with a treatment system, e.g., a device that doses a drug (e.g., insulin in the case of diabetes) or a device that otherwise influences the body (e.g., a device that provides an organ with a physical stimulation, e.g., electrical).

FIG. 5 is a schematic diagram illustrating a device and technique for optical excitation and detection of spatial coordinate parameters of tethered particles 500 whose spatial movement characteristics change between an unbound state 500 and bound state 504 in response the presence of a target analyte.

The device can represent different configurations, e.g., (i) plasmonic particles tethered to a substrate, whereby the plasmon resonance of the particles changes as a function of a coordination parameter with respect to the substrate, or (ii) scattering particles tethered to plasmonic particles that are rigidly attached to a substrate, whereby the plasmon resonance changes in dependence of the coordination of the scattering particle with respect to the plasmonic particle. Also, a plasmonic particle tethered to a plasmonic particle is a possible implementation, where the plasmon resonances change in dependence of changes of spatial coordinates between the two particles.

In the following, data is described for the binding of antibodies to plasmonic nanorods attached to a glass substrate, where the binding of antibodies changes the plasmon resonance of the nanorods. The data are illustrative for how single binding events (be it of antibodies, or of other particles free in solution, or of tethered particles) can be recorded and how many sensors can be monitored in parallel over time.

The tethered particles 500 are immobilized onto coverslips in a flow-cell 508. An illumination beam 510 from a laser 512 undergoes total-internal-reflection in the wall of cell 508 and excites plasmons in the particle 500. An optical scattering signal 514 of the tethered nanoparticle is directed to an optical detector 516, where it appears against a dark background, ensuring a high signal-to-noise ratio. Plasmon shifts will then result in changes of detected signal intensity. A processor 518 analyzes signals from detector 516 to determine spatial coordinate parameters of particles 500 which are indicative of the presence of target analyte.

The detector 516 may be an electron multiplying charge-coupled-device (EM-CCD) which can image many individual tethered particles. Alternatively, to reach microsecond integration times, the scattered intensity of a single tethered particle may be projected onto an analog photodiode.

The analyte biosensing technique allows for the sensitive detection of extremely small target concentrations. It has significant sensitivity by allowing for single-molecule detection. The selectivity is significantly higher than ensemble-averaged methods because single-molecule resolution allows for the discrimination between specific (strong, long-lived) and non-specific (weak, short-lived) interactions on a per-molecule basis.

Embodiments of the present invention may use techniques of dark field scattering spectroscopy. Specifically, it may use techniques using a bright low-temporal coherence light source, preferably with a line width larger than 5 nm (e.g., superluminescent diode) for dynamically measuring changes in the plasmon resonance peak of plasmonic particles.

Most detection methods for scattering objects such as metallic nanoparticles use dark-field illumination to obtain an image in which the object has a higher intensity than the background. For small particles (<100 nm in diameter for gold) the scattering signal reduces as the sixth power of the radius and quickly becomes swamped by the background. Imaging smaller objects therefore requires a high irradiance to obtain enough signal.

Imaging and/or spectroscopy of scattering objects is usually performed with a non-coherent white-light source (emission bandwidth >1000 nm). It allows for the imaging of scattering objects against a homogeneous and low background, and it can be used to extract a broadband scattering spectrum by determining the scattering signal at many different wavelengths using the same illuminator. Commonly employed sources are incandescent lamps (e.g., halogen) or arc-discharge sources (e.g., Xenon). The main disadvantage of these sources is their extended emitting area (>1 mm$^2$), which does not permit tight focusing of the beam to achieve a high irradiance of the sample.

One way to overcome this is by using a narrowband and coherent light source such as a laser. The high coherence and low bandwidth (typically <1 nm) allow for the tight focusing of the beam to achieve a high irradiance of the sample. However, coherent laser irradiation has limitations because (1) interference fringes cause an inhomogeneous illumination pattern and (2) small spurious reflections and leakage of light in the optical setup cause background artefacts in the image. Such artefacts significantly reduce the signal-to-noise ratio and may fluctuate in time due to vibrations and thermal drifts of the optical setup.

In such biosensing applications white-light sources or lasers are known to be useful to measure spectral shifts. White-light sources exhibit a spectral breadth B much larger than the line width Γ of a nanoparticle (i.e., B>>Γ), and thus allows for the measurement of the whole spectrum at once using a spectrometer. Shifts of the spectrum are then extracted by analyzing subsequent spectra. On the other hand, spectral shifts are also measured using a source that is much narrower than the line width of the particle, e.g., a laser (B<<Γ). The time-dependent scattered signal will change when the spectrum of the object shifts. However, because superluminescent diodes (SLDs) exhibit a spectral breadth that is similar to the line width of nanoparticles (i.e., B~Γ), the use of SLDs for dynamic spectral shift measurements on nanoparticles is unexpected. Optical coherence tomography also uses SLDs for illumination, but there is no intention to measure spectral changes of the sample. Although particles with different plasmon resonances are used, the resonance wavelength is fixed and does not change in time. Thus, the measurement of dynamic behavior of plasmons using an SLD is unexpected because it is not intuitive to choose for a light-source that has a bandwidth only slightly narrower than the line width of the resonance that is probed.

The line width of a metal nanoparticle is typically 40-50 nm. A white-light source such as a halogen lamp has a line width much broader than a nanoparticle. A laser has a line width much narrower than a nanoparticle, whereas the line width of a typical SLD is typically 15-30 nm, depending on the emission wavelength, which is comparable to the line width of a nanoparticle.

FIGS. 6A-B illustrate two implementations of a combined microscopy and spectroscopy method that use a bright and low-coherence light source, a superluminescent diode (SLD) 600, for the time-dependent imaging of scattering objects 602. In the biosensing techniques of embodiments of the present invention, the time-dependent signal represents shifts of the plasmon resonance peak of the scattering object indicative of the presence of an analyte. The shorter coherence length of the SLD light 604 compared to laser light significantly reduces the artefacts caused by interference, while the brightness of SLDs is similar to common diode lasers.

The low coherence and intermediate bandwidth (e.g., 15-30 nm at near-infrared wavelengths) of the beam result in homogeneous illumination and low background intensity. The high brightness and small emitting area (e.g., less than 30 μm$^2$ when coupled to a single-mode fiber) ensure a high irradiance. The scattering signal from an object illuminated with a superluminescent diode is high compared to the background and stable on short as well as long timescales.

In FIG. 6A the SLD 600 illuminates the sample 602 under an angle exceeding the angle for total internal reflection at a glass-water interface of a liquid cell 606. In this implementation, the light 604 is coupled to the sample 602 via a glass prism 608. In an alternate implementation, shown in FIG. 6B, the light 604 is coupled to the sample 602 via the back aperture of an objective lens 610. Because the implementation in FIG. 6A separates the excitation and emission light-paths, it leads to a lower background and higher signal-to-noise ratio than the implementation in FIG. 6B. The implementation in FIG. 6B may be useful if the space above the sample is to be used for other purposes, e.g., a technical component for temperature regulation. In both implementations, because the angle of illumination is higher than the angle for total-internal-reflection at the glass-water interface of the cell 606, all the excitation light is reflected. The presence of the particle 602 perturbs the total-internal-reflection, leading to a certain intensity of scattered light 612 that is partly collected by the objective and sent to an imaging sensor 614. The reflected beam is blocked by a beam-block, and the remaining scattered light is sent to an imaging detector 614, preferably a camera with sufficient dynamic range and wavelength sensitivity to achieve single-molecule resolution. In another embodiment, the sample 602 can be mounted on an optical probe (e.g., optical fibre or a waveguide) to allow for measurements to be conducted directly in complex biological environments. Signals from detector 614 are then analyzed by a processor 616 to determine the presence of the target analyte.

The assay may involve e.g., a binding assay, a competitive assay, a displacement assay, a sandwich assay, an enzymatic assay, an assay with target and/or signal amplification, a multi-step assay, an assay with molecular cascade, etc. The assay may involve recognition moieties of different natures, e.g., peptides, proteins, nucleic acids, carbohydrates, etc. Embodiments may include various calibration methods, controls, multiplexing, etc. Embodiments may include measures to block and reduce unwanted processes (e.g., non-specific processes that generate background signals) and to increase efficiency, stability, and selectivity of signal generation.

Embodiments of the present invention include a system and technique for biosensing an analyte in a matrix using a large collection of nanoscale detectors whose optical properties are individually altered in the presence of an analyte. In preferred embodiments, for example, a plasmonic biosensor based on hundreds of individual gold tethered nanoparticles with single-molecule sensitivity are simultaneously monitored in real-time within a dark-field microscopy setup.

A plasmonic biosensor may include hundreds of individual gold tethered nanoparticles with single-molecule sensitivity that are simultaneously monitored in real-time within a dark-field microscopy setup. The approach allows for the statistical analysis of single-molecule interactions without requiring any labeling of the analyte. The waiting-time distribution is concentration-dependent and obeys Poisson statistics. In one embodiment, the ability to probe hundreds of nanoparticles simultaneously provides a sensor with a dynamic range of 7 decades in concentration and will enable the study of heterogeneity in molecular interactions.

Single-molecule detection has distinct advantages over ensemble-averaged techniques because it yields statistical distributions of molecular properties instead of averages, and reveals rare and unsynchronized events. Preferred embodiments of the invention include techniques for monitoring hundreds of single-molecule plasmonic tethered nanoparticles in real-time using total-internal-reflection excitation in a standard microscope arrangement.

In one implementation of the embodiments shown in FIGS. 6A-B, the superluminescent diode is a Superlum, with center wavelength 795 nm, bandwidth 14 nm, maximum power 35 mW. The detector 614 is a charge coupled device (CCD), e.g., with an area of 50×50 $\mu m^2$ on the sample surface.

The density of particles on the substrate may be controlled by the concentration during spin coating to yield 150-250 particles in a 100×100 $\mu m^2$ field-of-view of the microscope. Each particle site exhibits a different scattered intensity caused by (a) the inevitable dispersion in particle volume and aspect ratio leading to a different scattering cross-section at the irradiation wavelength, and (b) a different orientation of each particle in the partly polarized evanescent field. To ensure that the technique probes single nanorods, white-light scattering spectra of all the particles are recorded. Less than 10% of the particles are in clusters, which are discarded in the analysis.

The use of a superluminescent diode (SLD) as the light-source is important to achieve sufficient signal-to-noise ratio (S/N). The poor spatial coherence of light from an incandescent lamp provided insufficient intensity to image the small particles, whereas the high temporal coherence of laser illumination resulted in interference artifacts that induce signal fluctuations. SLD's are semiconductor high-gain devices that generate amplified spontaneous emission. In this application the low temporal coherence of the SLD significantly reduced interference artifacts whereas the high spatial coherence ensured a high illumination intensity. This resulted in shot-noise limited signals for an integration time of 100 ms.

In a typical single-molecule experiment an analyte is passed into the flow cell using a syringe pump. The CCD camera is used to record the time-dependent scattered signal (determined by a two-dimensional Gaussian fit of each spot in each frame). Plasmon shifts associated with changes in tethered nanoparticle movement are then observed as stepwise changes in the normalized scattered intensity as a function of time using a step finding algorithm. Stepwise changes in the signal indicate stochastic binding of single antibodies (antibody concentration 10 nM). The sign of the stepwise changes depends on the plasmon wavelength relative to the wavelength of the irradiation source. The magnitude of the steps varies from 1% to 5%, with the variation of step-sizes indicating differences of position and orientation. The sign of the signal caused by analyte binding depends on the plasmon wavelength relative to the SLD wavelength. For particles with a plasmon wavelength shorter than the SLD wavelength the red-shift of the plasmon causes an increase in the scattered signal, whereas particles with a plasmon wavelength longer than the SLD wavelength exhibit the opposite behavior. A fraction of the particles does not exhibit step-wise changes of the signal because the plasmon wavelength is close to the SLD wavelength. For that reason the analysis may exclude particles with a plasmon resonance between 775 nm and 815 nm. It may also exclude steps with a S/N<2 (defined as the ratio between step-size and standard-deviation of the signal before analyte injection) which we attribute to drift of the background or analytes binding to the glass surface close to the particles.

From the step finding fit to the data the processor can estimate a value for ti, the mean waiting-time between steps. The distribution of waiting-times obeys Poisson statistics, with a mean binding rate that depends on the analyte concentration according to a power law, as shown in the graph of FIG. 7.

The detected scattered intensity is obtained by fitting a particle's diffraction-limited spot in each frame with a two-dimensional Gaussian. The S/N (defined as the ratio between the mean and the standard-deviation of the signal over 150 seconds) increases for brighter particles. The S/N approaches the shot noise limit with some excess noise that is likely caused by fluctuations of the SLD intensity and slight mechanical drift of the sample. From these measurements we conclude that step-wise signal-changes of 1% can be detected with a S/N of 3-5 for particles with an integrated intensity over $10^5$ counts/s.

The precision with which an analyte concentration can be determined is limited by counting statistics. For example, at least 100 molecules need to be detected in a defined time window in order to have a precision of concentration-determination of about $1/\sqrt{100}=10\%$. Small particles have a limited number of receptor molecules on their surface, so an individual particle can capture only a limited number of analyte molecules.

Furthermore, in the limit of very low analyte concentration, there is a high probability that a single particle will not have captured even a single analyte molecule, even for long incubation times. To address this issue, a biosensing system according to preferred embodiments of the invention have at least 100 tethered nanoparticles, and time traces are recorded on the individual particles. The data of the particles is combined by the processor in order to determine an analyte concentration. For low analyte concentration, preferably data is combined from at least 1000 particles, more preferably at least 10,000 particles.

Due to variations during the fabrication process of the nanoparticles, they may have variable distinct sizes, resulting in inconsistent spectral properties. To address this issue, it is preferable to use particles with an inherently narrow distribution of plasmon resonances, e.g., gold bipyramids. The inventors have found that the ensemble line-width of the extinction spectrum of a solution of bipyramids approaches the single-particle line width of 50 nm, whereas the ensemble line width of gold nanorods is typically ~200 nm.

This indicates that the individual bipyramids are optically more homogeneous. To address this issue it is also preferable to use a biosensing system with multiple wavelengths. A preferred solution is to record time-traces at a number of different wavelengths, e.g., using a wavelength-tunable superluminescent diode.

It is advantageous to have a biosensing system with a high number of particles. However, in a miniaturized system only a limited surface area is available. Furthermore, the density of particles on the surface is limited, because the optical system needs to be able to record time traces of individual objects. To address this issue, it is preferable to have system in which more than a predetermined fraction of the particles are separated from nearest-neighbor particles by at least the diffraction limit of the optical system. Another way to address this issue is to use an ordered pattern of particles on the surface, rather than a random distribution. Preferably the pattern of particles on the surface is conformal to the pattern of pixels on a digital camera chip. Digital cameras typically have rectangular pixels; for a camera chip with rectangular pixels, the particles are preferably situated on a rectangular grid. Another way to address this issue is to use an optical system in which a single particle maps onto a single pixel of a digital camera chip. Preferably, a single particle gives a signal on a single pixel that is at least 5 times higher than the signal on that pixel caused by neighbouring particles. Another way to address this issue is to use particles with different spectral properties, patterned in an alternating way on a surface, with a minimal spacing below the diffraction limit. Due to the different spectral properties, sub-populations of particles can be selected and time-traces can be recorded on different sub-populations with single-particle resolution, even if they are spaced by less than the diffraction length.

In a particle-based biosensing technology with optical detection and single-particle resolution, it is important to identify and ignore undesired particle-like objects that are sources of noise. Particle-like objects of this kind may be related to sample contamination or aggregates in the sample, or because of biochemical properties of sensing particles (e.g., surface functionalization), particle properties (e.g., shape, optical properties), or configurations of particles with other particles (e.g., multi-particle aggregate, or multiple particles in proximity that cannot be optically resolved). To address this issue, spectral properties of these particles can be recorded and compared to reference data. The spectral properties can be recorded, e.g., using a broadband light source and tunable filter, or using a source with tunable wavelength. Spectral signals can be used to identify unreliable objects caused e.g., by particle properties (e.g., shape) or particle configuration (e.g., clusters of particles). Individual tethered nanoparticles are characterized by a single narrow Lorentzian spectrum, allowing us to discard clusters based on the line shape and line width of the spectrum. Also, the scattering spectrum of clusters of nanoparticles exhibit a double peak or no clear peak at all. These clusters can easily be distinguished from the spectra of individual particles and are discarded from the data analysis.

Another technique to address this issue is to compare signal time-traces of individual objects with time-traces of a plurality of other objects. Objects having characteristics that strongly deviate from a plurality of other objects may be rejected, e.g., based on noise characteristics, drift, step sizes, number of steps, cumulative signal over a long time, etc.

The dynamic range of the sensor has low- and high concentration limits. Low analyte concentrations limit the statistics because the binding rate is low. For low concentrations, the minimum accessible concentration is determined by the number of particles in a field-of-view. The 2D Gaussian fitting algorithm currently requires a region-of-interest of 10×10 pixels to obtain an accurate fit for a magnification of 60×. High-end scientific cameras having a resolution of over 5 megapixels have an estimated number of particles of 50 in the field-of-view under optimum conditions. The lowest accessible concentration is then $c \approx 0.5$ pM. Higher analyte concentrations exhibit an increased rate of binding, for which a higher frame rate (i.e., a shorter integration time) is required to resolve all single-molecule binding events. Based on the Poisson distributed waiting times, a frame rate of $50/\tau$ will ensure that the short times in the distribution are also resolved. By increasing the incident intensity from 64 W/cm$^2$ to 1 kW/cm$^2$ the integration time is reduced to 6 ms with only a modest reduction in S/N. The maximum frame rate that can be achieved is fundamentally limited by the photo-thermal heating of the nanoparticles. For studies on biological samples the maximum permissible temperature rise is of the order of 10 K, which we estimate is reached for an incident intensity of 10 kW/m$^2$. This implies that a frame rate of 20 fps is achievable without inducing thermal damage to the analyte. Such high frame rates give access to low-affinity interactions or to analyte concentrations as high as about 5 µM.

Probes for biosensing with single-molecule resolution (e.g., a metal nanoparticle, a dielectric resonator, a solid-state nanopore) typically exhibit a limited dynamic range due to the low number of binding sites per probe, prohibiting the accumulation of sufficient statistics at low analyte concentrations. This limitation is overcome in embodiments of the present invention by the parallelized probing of many sensors, giving an extraordinary projected dynamic range of 7 decades in concentration. The ability to extract distributions of molecular interaction parameters enables the investigation of heterogeneity in a population of unlabeled molecules. The simple and cheap optical layout allows the sensor to be implemented easily with a microscope.

High analyte concentrations will give binding events with a high rate of binding. This makes it complicated to resolve individual binding events in measured time-traces. Also, low-affinity interactions can give rise to short-lived states which are difficult to resolve. To address this issue, it is preferable to use an optical system with a high frame rate. Preferably the frame rate or reciprocal integration time is higher than 100 s$^{-1}$, more preferably higher than 1000 s$^{-1}$.

The temperature of the particles is crucial because the structure and activity of the protein can be impaired when it is heated for extended periods of time. Most globular proteins exhibit a melting temperature ranging from 40° C. to 80° C. depending on pH and buffer conditions. Based on a theoretical model, it is estimated that an incident intensity exceeding 10 kWcm$^{-2}$ is needed to raise the particle temperature by more than 10 K.

A high signal-to-noise ratio and high frame rate can be achieved using a light source with high power. However, a high optical power can give an unacceptable temperature rise in the sample fluid, thereby affecting the biochemical materials. To monitor this potential issue, an optical thermometer may be integrated with the system. For example, using a phase-sensitive camera, or monitoring the blue-shifted emission from the metallic particles, may be implemented. To maintain an acceptable temperature the incident power can be adjusted.

A drift of optical signal from the particles due to binding and unbinding events complicates the observation of signals. To address this issue, it is preferable to use an internal reference to continuously or periodically calibrate the optical signal, e.g., a particle or another fiducial object with optical activity on the surface, which gives a stable optical scattering signal, without resonant properties and without sensitivity to molecular binding. The signal from a reference particle will be an optical reference for the illumination and detection status of the system. The reference signal can be used by the processor to correct for fluctuations in the optical signals from the biosensing particles, caused by drift in the components of the optical system and fluctuations of the intensity of the light source. The use of multiple reference particles on the surface will further improve the calibration. Examples of reference or fiducial markers are polystyrene spheres, nanopatterned surface structures, PDMS islands. Optical signal fluctuations can be caused by changes of optical path length, e.g., perpendicular to the imaging plane (z-axis). To address this issue, it is preferable to have an active z-axis feedback and control in the system.

Analyte multiplexing, i.e., measurement of different analytes at the same time, is advantageous for increased biomedical sensitivity and specificity. To provide for such multiplexing, some embodiments use particles that have different receptors on their surface. For reasons of counting statistics and precision, the number of particles should be at least equal to 100 for every analyte, and higher when necessary for an analyte with a low binding event rate (e.g., because it has a low concentration, or due to the affinity and density of the receptors). The minimal frame rate of the optical system is determined by the analyte with the highest (un)binding event rate. Also, some embodiments use particles with different optical properties, so that the different particles can be mixed. The particles preferably have at least two sub-populations that can be optically distinguished and that have different receptors on their surface. Also in this case, for reasons of counting statistics and precision, the number of particles is preferably at least 100 for every analyte, and higher for an analyte with a low binding event rate (e.g., because it has a low concentration, or due to the affinity and density of the receptors). The minimal frame rate of the optical system is determined by the analyte with the highest event rate.

According to some embodiments of the present invention, tethered particle motion (TPM) systems may be formed from a 50 nm long double-stranded DNA (dsDNA) tether that attaches a nanoparticle (e.g., microsphere or nanobead) of radius 500 nm to a substrate. In typical TPM systems the in-plane motion of this particle is tracked in time, so that a two-dimensional projection of the movement of the bead is obtained. When such a bead is repeatedly imaged within several consequent time intervals Δt, the combined result of all images results into a motion pattern. A distinguishing feature of the TPM method of the present invention compared to traditional TPM approaches is the fact that the system is designed so that the particle can bind to the surface, e.g., by coating both the bead and the substrate with complementary binding molecules. Thus, the tethered particle, which has a primary bond to the substrate via the tether, can form a secondary bond with the substrate. When such a secondary bond is formed, the motion pattern is significantly altered and can change its amplitude and/or symmetry. Moreover, the bound and unbound states are influenced by the presence of a target analyte, so that the presence of the analyte can be determined by measuring changes in the properties of the particle motion. Temporary changes in the motion pattern are indicative of the presence of the biomarker or analyte that one aims to probe, and therefore these changes are a measure of the concentration of this biomarker.

FIG. 8A is a schematic diagram of a tethered particle in an unbound state, while FIG. 8C is a schematic diagram of a tethered particle in a bound state. As shown in the plot of FIG. 8B, where each dot corresponds to a position of the particle in the x-y plane of the surface, the unbound tethered particle during a sampling period has a symmetrical distribution around the center axis (the center of the circle). As shown in the plot of FIG. 8D, the bound tethered particle during a sampling period has an asymmetrical distribution around the center axis (the center of the circle).

Embodiments of the invention may generally use any of various types of polymer (tether) with one end attached to a surface (substrate) and with the other end that is attached to an otherwise free bead (particle). The tethers may be, for example, double-stranded DNA, single-stranded DNA, or RNA, or a polypeptide, or another polymer. However, any polymer—or even, any macromolecule—that is able to attach a particle to a surface could in principle be used for TPM. Preferably, TPM systems of the present invention use double-stranded DNA (dsDNA) having a persistence length of approximately 50 nm.

A longer tether has the advantage that motion differences between bound and unbound states of the particle are large (so easier discrimination between bound and unbound states), and that a wide interaction area is probed between particle and surface (so more effective use of biofunctionalized surface area). A shorter tether has the advantage that the interaction rate (hit rate, effective concentration) between particle and surface area is high. Useful tether lengths are in the range between a few nanometers to a few micrometers, e.g., 5 nm to 10 micrometers.

In order to observe tethered particle movement on experimental timescales the size of the particle is preferably less than a few micrometers. Several types of particle may be used, including metal particles (e.g. gold), particles of organic or inorganic material, polystyrene particles, and fluorospheres. Comparing metal particles to polystyrene particles, an advantage of metal particles is the strong scattering of light. On the other hand, polystyrene particles are frequently used in optical tweezer experiments and enable magnetic control of the particle when including a magnetic core.

A larger particle has the advantage of higher optical signal and lower motion blur (so higher localization accuracy). A smaller particle has the advantage of a higher diffusivity and more rapid motion, for a higher interaction rate between particle and surface, and so that the change in mobility due to an analyte mediated bond has a higher time resolution. Useful particle sizes are in the range between a few nanometers to a few micrometers, e.g., 5 nm to 10 micrometers.

In preferred embodiments, the position of the particle is tracked by dark field microscopy, which results in data of the particle-center coordinates of X and Y parallel to the substrate, i.e., the 2D-projected motion of the bead. In some embodiments, the Z-coordinate of the particle may also be tracked, e.g., using diffraction signals.

In some embodiments, magnetic particles are used that consist of a polymer matrix with many small magnetic iron oxide ($Fe_2O_3$) grains. Magnetic particles can be actuated with a magnet and can be detected with standard light microscopy.

In one embodiment, the parameters used to characterize the dynamics of the system are the autocorrelation of the in-plane vector $\vec{R}(t)$ that describes the positions of the particle, $$<\vec{R}(t) \cdot \vec{R}(t+\tau)>$$

The characteristic time $\tau_1$ is defined as the time corresponding to the autocorrelation function of the in-plane vector $\vec{R}(t)$ that describes the positions of the bead. For example, in some embodiments, the value for $\tau_1$ is $(0.09\pm0.01)$ s, or more generally, $\tau_1$ is in the range from 0.1-0.3 s.

Binding moieties that may be used in the biosensor are e.g., proteins, antibodies, antibody fragments, recombinant proteins, saccharides, molecularly imprinted polymers, small molecules, nucleic acids, DNA, aptamers, multivalent binders, and combinations thereof.

Binding moieties are coupled to the particles and the surface preferably in the region where the two objects interact, i.e., in areas where the particle and surface have a nonzero hit rate. Moieties can be positioned close to or further away from the tether attachment points. The change of motion pattern between unbound and bound depends on the location where binding takes place. E.g., a binding between patches at the two respective tether attachment points gives a small centered motion pattern, whereas a binding between patches at the periphery of the interaction areas on particle and substrate give an off-centered motion pattern. Therefore, the pattern in the bound state is influenced by the location of the binders on the particle and on the substrate, and by the location where the analyte binds. Therefore, it can be advantageous to have a lookup table with possible bound motion patterns and relate a measured motion pattern to the data in the lookup table, so as to detect with good sensitivity the occurrence of particle binding.

The optimal density of binding moieties on particle and substrate depends on the type of assay and on the concentration of analyte. For example, in a sandwich assay with very low analyte concentrations, it is beneficial to have a high density of binding moieties on particle and substrate, in order to have good kinetics and a good sensitivity. A high density may be e.g., between $10^3$ and $10^5$ moieties/$\mu m^2$. In a competitive assay, at least one of the respective binding moieties should have a low surface density in order to avoid too strong multivalent binding between particle and surface, otherwise the analyte molecules cannot effectively displace the bindings in order to bring the particle in an unbound state.

The spacing between particles on the surface should be large enough so that the particles do not hinder each other's motion, and large enough so that the particles can be detected independent of each other, and small enough so that a high number of particles can be fitted on the sensing surface for optimal statistics.

According to embodiments of the invention, the preparation of the biosensor can be divided into several steps. A first step is to clean the bare sample. During the second step the surface and the particles are functionalized. A third step is to couple the functionalized particles to the functionalized surface. A fourth step can be to preserve the surface for further use, e.g., by coating the surface with a protective sugar-containing or another hydrophilic coating that dissolves when fluid is added to the sensor. Alternatively, the sensor surface may be coated with a hydrogel which protects the biochemical moieties and passes analyte when the sensor is in contact with a fluid sample. Many more methods and procedures exist to prepare a biosensor device, which are well-known in the art.

Biosensing systems according to the present invention can be used for in-vitro applications, or for in-vivo applications, or very generally for testing of the human body. It may be used as part of a medical device such as a catheter, a patch, a tube, a needle, a fiber, a clip, a wire. It may be used to support medical treatment, or as part of a device for monitoring in or on the body. It can be used in a disposable format such as a cartridge, a tube, a titer plate.

In in-vivo applications, the probes may be in interaction with the biological system via a filter module (e.g., a coating that passes analyte of interest and hinders passage of other components) and/or via a material that ensures biocompatibility and good operation while in contact with the live system.

Embodiments may include various additional features, including various forms of multiplexing, e.g., analyte multiplexing, spatial multiplexing, spectroscopic multiplexing, probe functionality multiplexing. Embodiments may include parallelization of probes, for statistics or for dynamic range (e.g., different probe functionalizations, multiplexed in position and/or in optical property). Embodiments may include various probe coatings, probe coverages, various ways and materials to embed and locate the probe in a matrix, analyte separation components, cell separation components, for specificity and/or sensitivity, which is particularly important in complex biological systems.

Embodiments may include an analyzer or readout instrument, which sends excitation into the sensor (e.g., optical, electrical, acoustic) and/or receives signals from the sensor and performs signal processing. The analyzer may also be used to transmit signals to other instruments and/or to a remote communication, processing and/or storage systems.

In one specific embodiment, the biosensor is based on hundreds or thousands of individual particles, with single-particle and single-molecule sensitivity, that are simultaneously monitored in real-time within a dark-field microscopy setup. The technique allows for the statistical analysis of single-molecule interactions without requiring any labeling of the analyte. The ability to probe hundreds of nanoparticles simultaneously provides a sensor with a large dynamic range. The biosensor is part of a biosensing system that overcomes limitations in the prior art by monitoring many single-particle sensors in real-time.

Data Acquisition

To obtain information about the motion of the particles in the assays, the particle motion is tracked. The particles are preferably but not necessarily imaged with dark field optical microscopy.

The raw camera image data is processed into the motion patterns of all particles in the field of view. For example, by calculating the square root of the length of the eigenvectors of the covariance matrix of the motion pattern, the standard deviation of the data points along minor axis and major axis are determined. The symmetry of the motion pattern is defined as the ratio of minor amplitude over major amplitude. The minor motion amplitude and the symmetry of the motion pattern may be used for ordering the motion patterns and for tracking the particle behavior as a function of time. Further data processing is done to reveal the number of binding and unbinding events and therefrom deduce the analyte concentration.

Figure 9A:
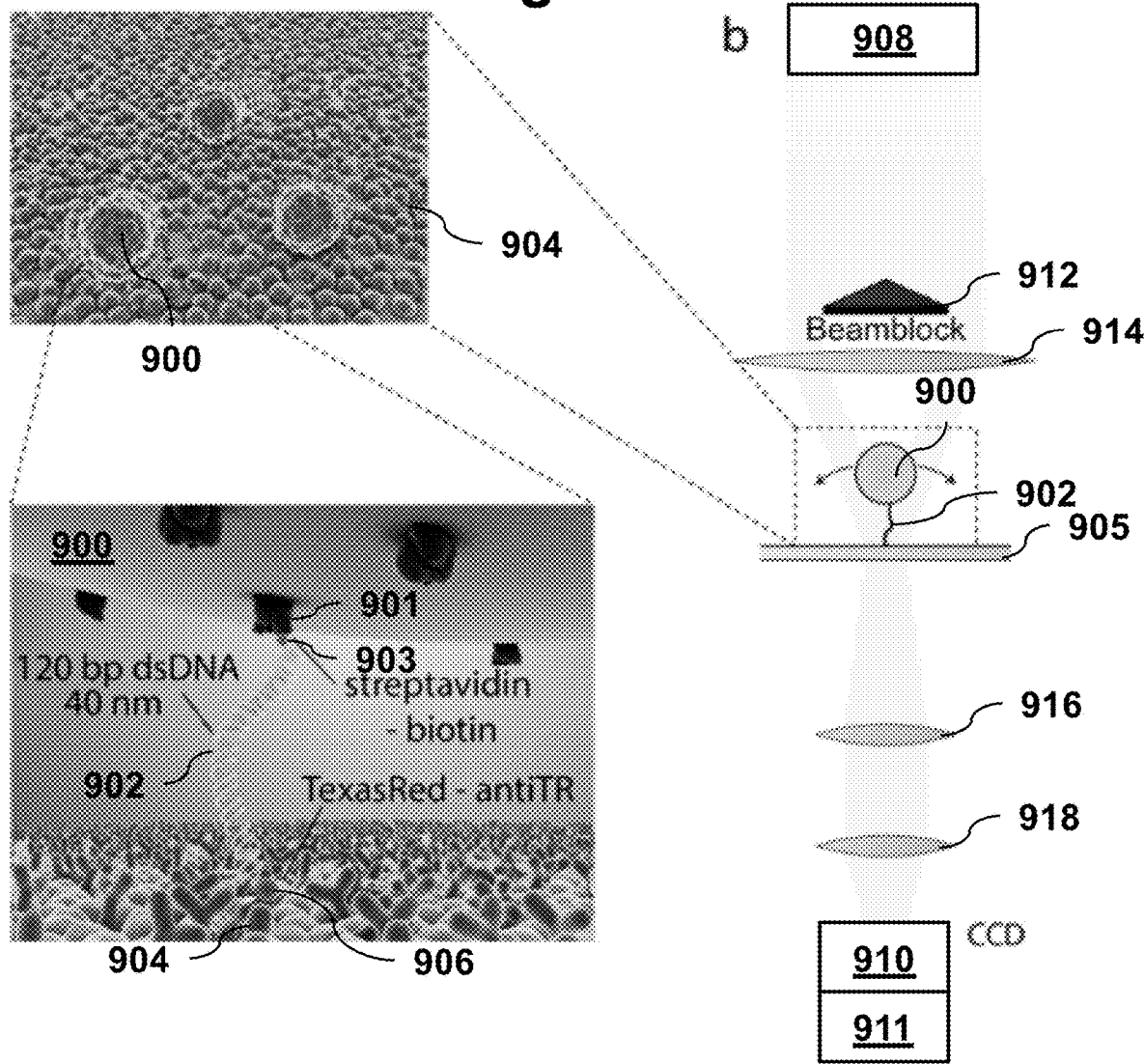
FIG. 9A shows a biosensing apparatus for particle motion measurement, according to an embodiment of the invention.
Figure 9B:
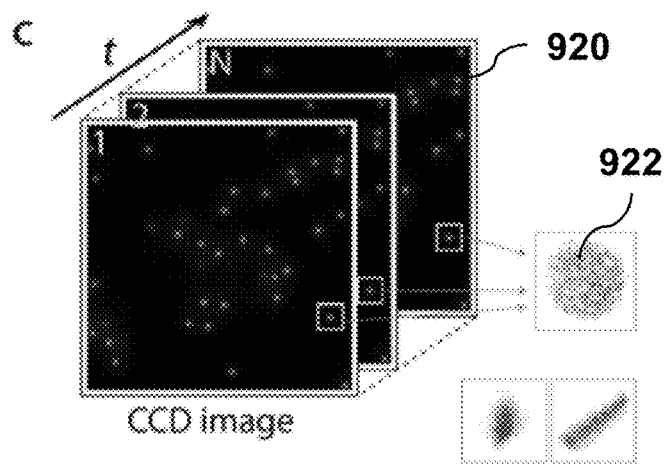
FIG. 9B shows a series of images of particle positions which are analyzed to determine particle motion patterns, according to an embodiment of the invention.

An apparatus for particle motion measurement according to one embodiment is illustrated in FIG. 9A. Particles 900 are tethered to a substrate by 40 nm dsDNA tethers 902. The molecular tethers are functionalized on one end with biotin for binding to streptavidin 901 that is coated on particles 900, and on the other end with Texas Red 906 for binding to surface-coupled anti-Texas Red antibodies 904. Particle motion is recorded in a dark-field microscopy arrangement, with a white light source 908 and CCD camera 910. The imaging apparatus include a beam block 912 and lenses 914, 916, 918. Images captured by camera 910 are analyzed by processor 911. A series of images 920 are collected, as shown in FIG. 9B, and analyzed to locate particles in every frame. The corresponding motion pattern is constructed as a dot plot 922.

The short tether 902 keeps the particle 900 close to the substrate 905 and thereby ensures high-frequency sampling of the particle-substrate interaction. Through analysis of particle dot plots 922, a variety of motion patterns may be resolved with a localization accuracy of a few nanometers. The deviant motion patterns are associated with variations in the number and orientation of the tethers, particle roughness and bindings between particle and surface.

As an illustrative concrete example, we now describe one specific implementation. To provide functionalized substrate 905, glass coverslips (Menzel-Gläser, Germany) were cleaned by 5 minute sonication in aceton, isopropyl alcohol and methanol baths. Substrates were dried between each step using a gentle stream of nitrogen and stored under vacuum in a desiccator until use. Fluid cells (Grace Biolabs) with a volume of 23 µL, were attached to the functionalized substrate using an adhesive layer. Functionalization of the substrate was performed by physisorption of anti-TexasRed antibodies to the glass. Antibodies were diluted in PBS to the desired concentration (8-5000 ng/mL) and incubated for 60 minutes in the fluid cell, followed by substrate blocking using 5 minute incubation of 1 wt % BSA in PBS. The fluid cells were flushed with 1 mL PBS after each incubation step.

To provide particle functionalization with DNA, streptavidin-coated superparamagnetic particles (MyOne Streptavidin C1, Life Technologies) were incubated with 120 bp dsDNA at a ratio of 10 to 2000 dsDNA per particle. Double stranded DNA of 120 bp in length with a biotin molecule on one end and a TexasRed dye molecule on the other end have been obtained commercially from Ella Biotech (Martinsried, Germany). The concentration of particles during the 60 minute incubation was 8.3 pM in PBS buffer. The biotin moiety on the DNA binds to the streptavidin molecules during the incubation. The efficiency of this coupling reaction was determined to be approximately 70% by a supernatant assay. The supernatant assay quantifies the concentration of unbound DNA in the reaction supernatant using the fluorescent signal of the DNA intercalating dye SYBR-Green (see supplementary data for more details). After magnetic separation the particles were washed in PBS and finally suspended in 1 wt % BSA in PBS to a final concentration of 140 fM.

The dsDNA functionalized particles were bound to the antibody coated substrate by incubating the diluted particles in the fluid cells for 5 minutes. The TexasRed ends of the DNA tethers bind to the TexasRed antibodies on the substrate and create the particle-tether-substrate system as illustrated in FIG. 1a. The sample was turned upside down and stored for 10-30 minutes in order to remove unbound particles from the substrate through sedimentation.

Smooth polystyrene (PS) particles with a diameter of 500 nm (Microparticle GmbH, Germany) were functionalized with antibodies against biotin. The particles were functionalized with 120 bp dsDNA using the same protocol as for the MyOne particles (see above). Sedimentation of the PS particles is slower because the mass density is lower and the diameter is smaller than of the MyOne particles. Therefore, an incubation time of 15 minutes was used for the PS particles.

Samples were studied on an inverted Nikon Ti-E microscope (Nikon Instruments Europe BV, Netherlands) as illustrated in FIG. 9A. The particles were observed at a total magnification of 200× and illuminated using a dark field condenser; particles appear as bright spots on a low intensity background. A field-of-view (FOV) of 415×415 µm² can contain between a few to several thousand particles. The particles were recorded for 60 seconds at a sampling rate of 30 Hz as illustrated in FIG. 9B.

In post-processing by processor 911, the background light was removed using a low-pass wavelet based frequency filter. The location of individual particles was determined by calculating the center-of-intensity of the scattered light spots. Other possible processing techniques include, e.g., Fourier, Wavelet, and Threshold filtering. Particle locations in subsequent frames were correlated to yield the trajectories $\vec{X}(t)$. The average absolute position $\overline{X}$, was subtracted for each particle to yield the relative trajectories $\vec{x}_i(t)$.

A slight sample drift occurs during the experiments on the microscope. The drift of the sample was corrected by identifying a population of static particles that served as reference. Static particles were defined as particles with similar motion trajectories identified by applying a threshold p in the maximum difference in the relative trajectories max$|\vec{x}_i(t) - \vec{x}_j(t)| < p$ for all $i \neq j$. The threshold p was chosen to minimize the estimated error induced by the drift correction: $\sigma_{error} \propto p/\sqrt{N(p)}$ where N(p) is the number of particles classified as static for the selected threshold. The drift of the sample was determined from the average motion of these static particles and a low-pass wavelet filter was applied to suppress high frequency noise and Brownian motion contributions. The trajectories determined from the raw data were then corrected for the observed sample drift.

The positioning accuracy was determined to be less than 3 nm for the 1 µm magnetic particles. The positioning accuracy of the PS particles is expected to be very similar since the optical scattering signals of the magnetic and PS particles are comparable.

Figure 10:
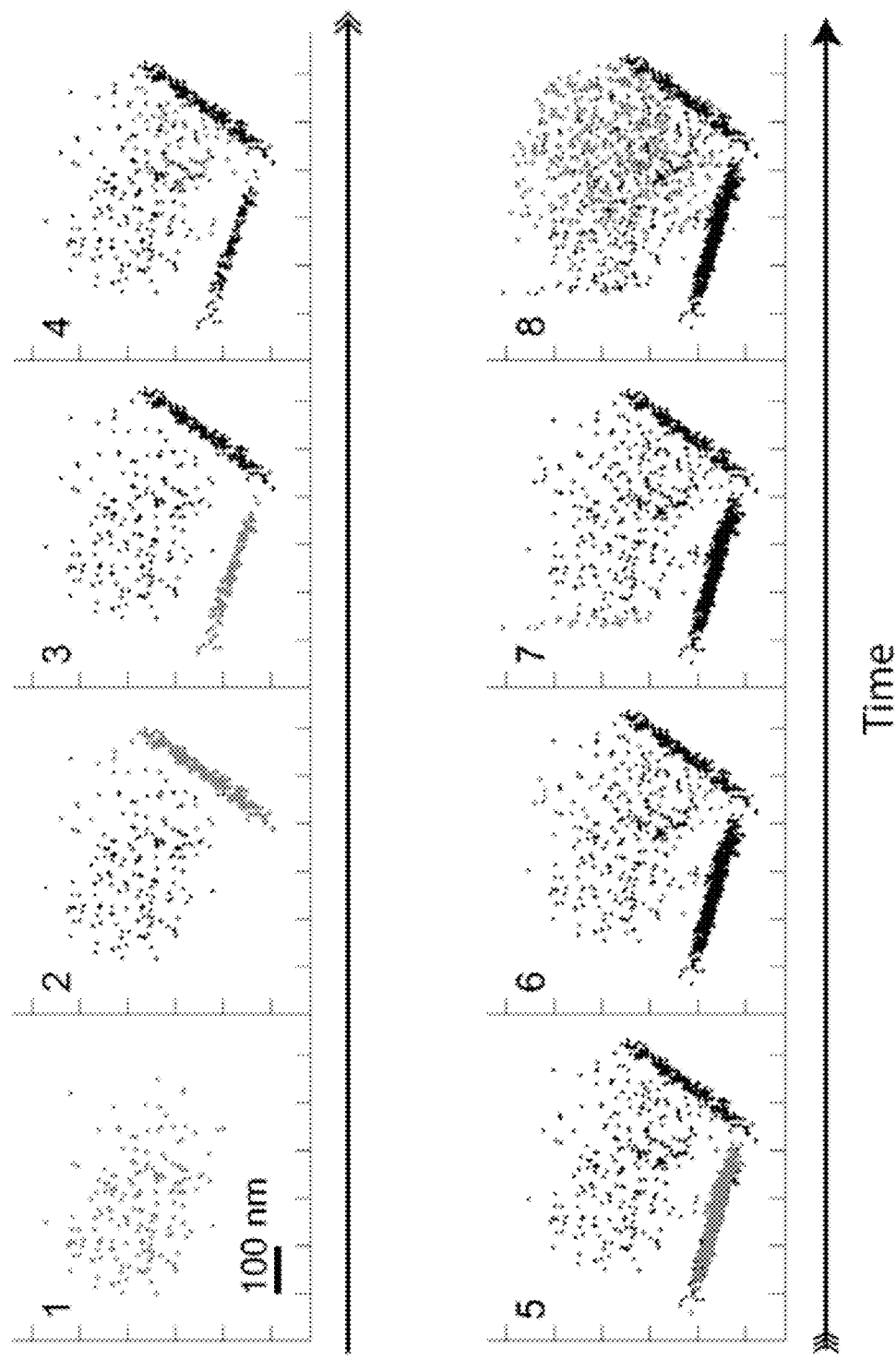
FIG. 10 shows a sequence motion patterns of a particle indicating transitions between an unbound and two bound states, according to an embodiment of the invention.

FIG. 10 illustrates a sequence of distinct time-dependent motion patterns of a particle. The figure shows a cumulative position scatter plot for a particle that alternates between a disc motion pattern and multiple-stripe motion patterns. The figure shows eight consecutive time intervals. In each frame, the newly collected points are indicated in gray, and previously collected points in black. The particle is initially observed in frame 1 to exhibit a disc pattern indicating an unbound state of the particle. The stripe pattern in frame 2 indicates a state where the particle is bound to the surface at a first location, and the differently oriented stripe in frame 3 indicates a state where the particle is bound to the surface at a second location. These bound and unbound states accumulate in subsequent frames 4, 5, 6, 7, 8. This experiment demonstrates that transitions can be measured between different binding states of particle and surface. The states are reversible and repeatable. The states indicate the presence of secondary bindings, in addition to the primary tether.

The particles of interest are those that show changes of motion pattern and correspond to a changing type of motion in the course of time. By analyzing the motion of these particles, the time spans where a particle is in the bound state or in the free state can be determined. We now provide a description of two methods of analyzing time-dependent motion: the step size function and the area function.

The step size can be used to quantify the diffusive motion of the tethered particle. Specifically, diffusive motion is determined by calculating the absolute distance that a tethered particle travels in a certain time interval, the step size. The step size is calculated as Step size $(t) = |r(t+\Delta t) - r(t)|$, where r is a vector. The step size as a function of time shows a significant amount of variation, an intrinsic aspect of Brownian motion. The result is a broad distribution of step sizes. The amount of variation in the step size can be suppressed by averaging the step size during a certain time window and shifting this window along the time axis. Drops in the step size indicate a binding event. To decrease the amount of fluctuations in the step size data, the step size is averaged over a window. To quantify the fluctuations, the standard deviation of the step size in each window is calculated. When increasing the window size, the amount of fluctuations decreases as expected. However, increasing the window size also leads to a decrease in the time resolution. There is thus a trade-off between amount of statistical fluctuations and time resolution. The preferred averaging time-window depends e.g., on the size of the particle. E.g., for a 1 micrometer diameter particle, an averaging-window size of 0.1-10 s is preferable.

To increase the contrast between the step size of the particle in the free and the bound state, the time interval over which the step size is calculated is varied. In the bound state the motion is not limited by the time interval over which the step size is calculated, but it is limited by the confinement of the freedom of motion due to the molecular bond. A contrast in the step size is defined as the average step size in the free state divided by the average step size in the bound state, as a function of the time interval Δt. The contrast increases as a function of the Δt, but the time resolution will decrease with Δt. The contrast will converge to a maximum value, as the particle in the free state is limited by the tether.

Figure 11A:
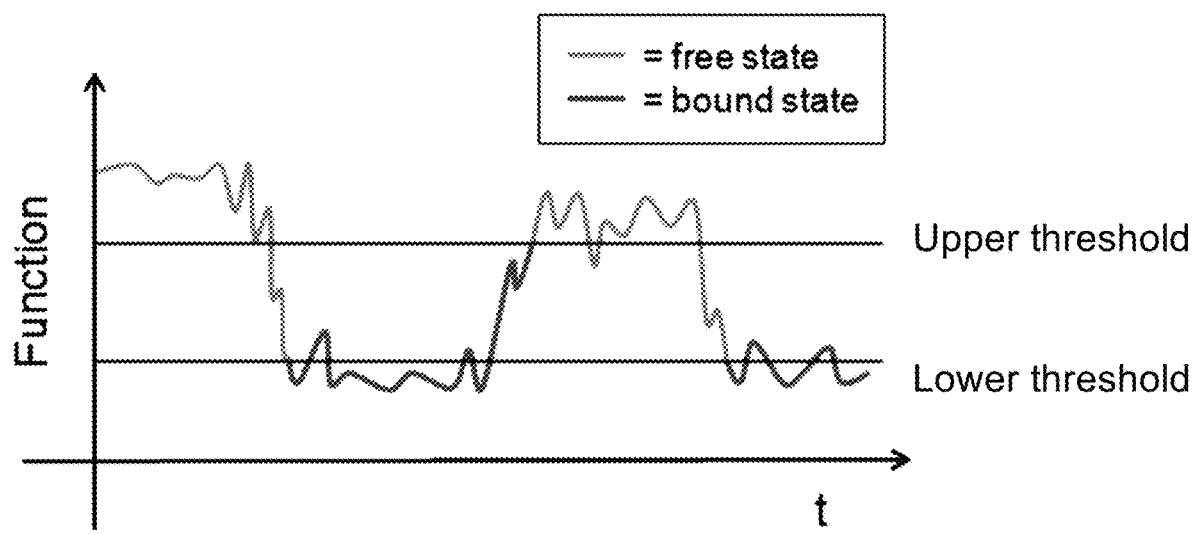
FIG. 11A shows a graph of the step (or area) function with respect to time, indicating two thresholds used to detect changes between bound and unbound states, according to an embodiment of the invention.
Figure 11B:
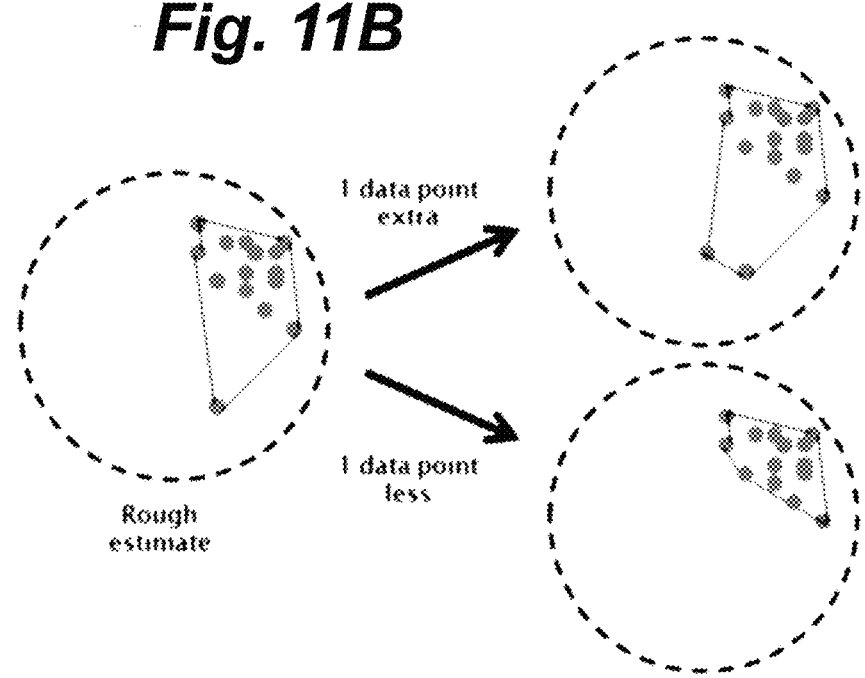
FIG. 11B shows the convex hull associated with a collection of position points for different time windows, according to an embodiment of the invention.

When a particle is in the bound state, the motion of a particle is more strongly confined compared to the motion of a particle is in the free state. Both the step size of the particle and the area that the particle probes decrease in the bound state. To represent the area that a particle probes as a function of time, the convex hull is calculated for a shifting window, as shown in FIG. 11B. This is called the area function. The area function may be calculated for a range of window sizes. As the window size is increased from a fraction of a second to several seconds, the area is calculated over more data points and the area function in the free state increases. However, when the system is in the bound state, the area increases significantly less. This is because in the bound state less time is required for the particle to probe its available phase space. So calculating the area over a longer time than the system needs to probe the phase space will not lead to a larger area. For the free state, the system is still in the regime where the particle does probe a larger area when increasing the window size. The contrast between the free state and the bound state increases as a function of the window size. Again the side effect of increasing the window size is losing time resolution. The same window size as for the step size may be used in the algorithm to distinguish bound and unbound states. FIG. 11B illustrates that a larger change in the area function is associated with addition or removal of a data point far away from existing data points in a window.

The decrease in the step size and the area function when a tethered particle makes a molecular bond is not always equal. This decrease depends on the position of the molecular bond relative to the tether.

The goal of analyzing the motion of the particles is to discern binding events in the observed motion of the tethered particles.

After having performed the raw data analysis, the trajectories of all particles are known. Of these trajectories the ones that correspond to single tethered particles are of particular interest. The first step is to filter out all uninteresting motion patterns. By setting thresholds on both the minor amplitude and the symmetry of the motion patterns, a large group of uninteresting motion patterns may be filtered out. The used thresholds are preferably as follows: symmetry >0.75, and 50<minor amplitude <175 nm for a short tether system, and symmetry >0.85, and 125<minor amplitude <225 nm for the long tether system. Yet these thresholds are just indications and can be optimized for the relevant systems. The ring- and bell-shaped motion patterns that meet the selection criteria can be discarded, but this is not absolutely necessary.

Of each selected trajectory, the state of the tether-particle system as a function of time, represented by the state vector, is calculated. The state vector is defined as a list of zeros and ones where a one corresponds to the system being in the bound state and a zero corresponds to the free state. The algorithm first calculates a rough estimate of the state vector by looking at both the step size function and the area function. With each function the motion is analyzed and the state of the system is determined by setting two thresholds, an upper threshold and a lower threshold, as shown in FIG. 11A, which is a graph of the step (or area) function with respect to time. A transition of the function below the lower threshold is used to detect a change in state from free to bound, a binding event. A transition of the function above the upper threshold is used to detect a change in state from bound to free, an unbinding event. Two different thresholds are used so that the state detection is less sensitive to statistical fluctuations, because only very large increases or decreases are detected. Only in the frames where both functions regard the system to be in the bound state, the state vector is set to one. The upper and lower thresholds for both functions are chosen such that the lower threshold is at a higher level than the level of the bound state and the upper threshold is about 1 sigma below the level in the free state. The thresholds are different for the two model systems because the dimensions of the systems are different.

The third and last step is to determine the exact start frame and end frame of each bound period.

The system may also be equipped with a method to apply force to the particles, e.g., based on magnetic force, optical force, or acoustic force. The application of force can help to discriminate between bound and unbound particles, or to influence the kinetics and/or the equilibrium between bound and unbound states, thereby improving the sensitivity, specificity and/or speed of biosensing.

The features described in various separate embodiments of the invention are not necessarily exclusive and, in general, may be used in combination with each other. Such features and embodiments also include material disclosed in U.S. provisional patent applications 62/092,751 filed Dec. 16, 2014, 62/092,763 filed Dec. 16, 2014, and 62/132,096 filed Mar. 12, 2015, all of which are incorporated herein by reference.

The invention claimed is:

1. A biosensor for sensing an analyte using tethered particle motion, the biosensor comprising:
   a particle;
   a surface;
   a tether molecule bound at a first end to the particle and bound at a second end to the surface;
   a first moiety bound either to the particle or to the tether molecule;
   a second moiety bound either to the surface or to the tether molecule;
   wherein first moiety is bound to the particle and/or the second moiety is bound to the surface;
   wherein 1) the first moiety and the second moiety have a binding affinity to each other in dependence on the presence or absence of a target analyte, and/or 2) the first moiety and the second moiety have a binding affinity to the target analyte;
   whereby motion characteristics of the particle change depending on the presence of the analyte, thereby allowing sensing of the analyte by measuring changes in a spatial coordinate parameter of the particle relative to the surface.

2. The biosensor of claim 1 wherein the surface is the surface of a substrate.

3. The biosensor of claim 1 wherein the surface is the surface of a second particle.

4. The biosensor of claim 1 wherein the particle has a size in the range 5 nm to 10 μm.

5. The biosensor of claim 1 wherein the tether molecule has a length in the range 5 nm to 10 μm.

6. The biosensor of claim 1 wherein the biosensor has a density of binding moieties in the range between $10^3$ and $10^5$ moieties/μm$^2$.

7. The biosensor of claim 1 wherein moieties bound to the particle or to the surface have a density of up to $10^5$ moieties/μm$^2$.

8. The biosensor of claim 1 comprising at least 100 particles bound to first ends of at least 100 corresponding tether molecules that are bound at second ends to the surface.

9. The biosensor of claim 1 wherein the biosensor has 2-10,000 particles in a 415×415 µm² region.

10. The biosensor of claim 1 further comprising an optical system having a diffraction limit, wherein the biosensor comprises tethered particles separated from nearest-neighbor tethered particles by at least the diffraction limit of the optical system.

11. The biosensor of claim 1 further comprising an optical system having a diffraction limit, wherein the biosensor comprises tethered particles with different spectral properties patterned in an alternating way on the surface with a minimal spacing below the diffraction limit.

12. The biosensor of claim 1 further comprising a digital camera having a pattern of pixels, wherein the biosensor comprises tethered particles patterned on the surface to conform to the pattern of pixels.

13. The biosensor of claim 1 wherein the biosensor implements a binding assay, a competitive assay, a displacement assay, a sandwich assay, an enzymatic assay, an assay with target and/or signal amplification, a multistep assay, or an assay with molecular cascade.

14. The biosensor of claim 1 wherein the first moiety or the second moiety is a protein, an antibody, a fragment thereof, a recombinant protein, a carbohydrate, a saccharide, a molecularly imprinted polymer, a small molecule, a nucleic acid, a DNA molecule, an aptamer, a multivalent binder, or a combination thereof.

15. The biosensor of claim 1 wherein the first moiety or the second moiety is a glucose binding molecule.

16. The biosensor of claim 1 adapted to perform multiplexing, analyte multiplexing, spatial multiplexing, multiplexing in position, particle-based multiplexing, particles with different optical properties, use of multiple wavelengths, spectroscopic multiplexing, particles that have different receptors on their surface, probe functionality multiplexing, different probe functionalizations, various probe coatings, various probe coverages, various probes in a matrix, or combinations thereof.

17. The device of claim 1 used for in-vivo biosensing, ex-vivo biosensing, or in-vitro biosensing.

18. The device of claim 1 used for in-vitro diagnostic testing, point-of-care testing, environmental testing, food testing, forensics, biological, biomedical, and pharmaceutical research, or to monitor assays with live cells, tissue, or organs.

19. The device of claim 1 used as a sensor on or in or as part of an endoscope, a tube, a needle, a fiber, a catheter, a patch, or a disposable probe, or a disposable cartridge.

20. A method for sensing an analyte using tethered particle motion, the method comprising:
providing a biosensor comprising:
a surface;
a tether molecule bound at a first end to the particle and bound at a second end to the surface;
a first moiety bound either to the particle or to the tether molecule;
a second moiety bound either to the surface or to the tether molecule;
wherein first moiety is bound to the particle and/or the second moiety is bound to the surface;
wherein
1) the first moiety and the second moiety have a binding affinity to each other in dependence on the presence or absence of a target analyte, and/or
2) the first moiety and the second moiety have a binding affinity to the target analyte; and
detecting motion characteristics of the particle that change depending on a presence of the analyte, wherein the motion characteristics comprise a spatial coordinate parameter of the particle relative to the surface.

* * * * *